United States Patent [19]
Coy et al.

[11] Patent Number: 5,847,066
[45] Date of Patent: Dec. 8, 1998

[54] ANALOGS OF GROWTH HORMONE-RELEASING FACTOR

[75] Inventors: David H. Coy, New Orleans; William Murphy, Slidell, both of La.

[73] Assignee: The Administrators of the Tulane Educational Fund, New Orleans, La.

[21] Appl. No.: 631,421

[22] Filed: Apr. 12, 1996

Related U.S. Application Data

[63] Continuation-in-part of Ser. No. 524,337, Sep. 6, 1995, which is a continuation-in-part of Ser. No. 421,987, Apr. 14, 1995.

[51] Int. Cl.$^6$ .............................. A61K 38/00; C07K 5/00; C07K 7/00
[52] U.S. Cl. .......................... 530/324; 530/313; 530/325; 530/326
[58] Field of Search .............................. 514/12; 530/313, 530/324, 325, 326

[56] References Cited

U.S. PATENT DOCUMENTS

| | | | |
|---|---|---|---|
| 4,617,149 | 10/1986 | DiMarchi et al. | 530/324 |
| 4,649,131 | 3/1987 | Felix et al. . | |
| 4,689,318 | 8/1987 | Kaiser et al. . | |
| 4,734,399 | 3/1988 | Felix et al. . | |
| 5,002,931 | 3/1991 | Rivier et al. | 514/12 |
| 5,262,519 | 11/1993 | Rivier et al. | 530/324 |
| 5,416,073 | 5/1995 | Coy et al. | 514/12 |

FOREIGN PATENT DOCUMENTS

| | | | |
|---|---|---|---|
| 0 188 214 A2 | 7/1986 | European Pat. Off. | C07K 7/00 |
| WO 91/16923 | 11/1991 | WIPO | A61K 37/43 |

OTHER PUBLICATIONS

Cervini et al., "A SAR Study of the Complete Ala and Partial Aib Scans of the Growth Hormone Releasing Factor: . . . ", Peptides, Chemistry & Biology, Proceedings of 12th American Peptide Symposium Jun. 16–21, 1991.

Coy et al., "Differential Effects of N–Terminal Modifications on the Biological Potencies of Growth Hormone Releasing Factor Analogues with Varying Chain Lengths", J.Med. Chem., 30:219–222, 1987.

Felix et al., "Synthesis and Biological Activity of Novel Linear and Cyclic GRF Analogs", Escom Science Publishers B.V.: Leiden, Netherlands Illus. ISBN 90–72199–01–4.0(0), pp. 465–467, 1988.

Ling et al., "Synthetic GRF Analogs as Competitive Antagonists of GRF", Symposium Quo Vadis, Sanofi Group, May 29–30, 1985, France, pp. 309–322.

Ling et al., "Synthesis and In Vitro Bioactivity of C–Terminal Deleted Analogs of Human Growth Hormone–Releasing Factor", Biochemical & Biophysical Research Comm., 123:854–861, 1984.

Rivier et al., "Characterization of a Growth Hormone–Releasing Factor from a Human Pancreatic Islet Tumour", Nature vol. 300:276–278, 1982.

Wehrenberg et al., "Growth Hormone–Releasing Factor: A New Chapter in Neuroendocrinology", Hormone Res. 24:82–90, 1986.

*Primary Examiner*—Avis M. Davenport
*Attorney, Agent, or Firm*—Fish & Richardson P.C.

[57] ABSTRACT

A peptide which is a variant of the human growth hormone-releasing factor. The peptide, containing 23–28 amino acid residues, differs from its native counterpart at least at positions 8, 9, 16, 18, 24, 25, 27, and 28, and is potent in stimulating the release of growth hormone.

23 Claims, No Drawings

ANALOGS OF GROWTH HORMONE-RELEASING FACTOR

CROSS REFERENCE TO RELATED APPLICATIONS

This application is a continuation-in-part of U.S. patent application Ser. No. 08/524,337, filed on Sep. 6, 1995 now pending, which is a continuation-in-part of U.S. patent application Ser. No. 08/421,987, filed on Apr. 14, 1995 now pending.

STATEMENT AS TO FEDERALLY SPONSORED RESEARCH

Work described herein was supported in part by National Institutes of Health Grant DK-30167. The United States government therefore has certain rights in this invention.

BACKGROUND OF THE INVENTION

Growth hormone (GH) or somatotropin is a 191-amino acid peptide which is secreted by the anterior pituitary. Growth hormone itself does not promote growth directly, but acts by stimulating the production of growth factors, such as the somatomedins produced by the liver. The ultimate effects of growth hormone is to stimulate the growth of the skeleton, connective tissue, muscles, and viscera. Inadequate levels of growth hormone in children cause retardation of growth. It also causes retarded development of secondary sexual characteristics, impaired development of larynx, and hypoglycemia.

The production of growth hormone is under the control of both releasing and inhibitory factors secreted from the hypothalamus. The primary releasing influence is effected by growth hormone-releasing factor (GRF), which is produced primarily in the arcuate nucleus of the hypothalamus and transported to the pituitary by portal circulation.

Substantial efforts have been devoted to development of synthetic GRF analogs with greater efficacy than native GRF in stimulating release of growth hormone. For structures of human GRF (hGRF) and GRF's of other sources, see Wehrenberg, W. B., et al., Hormone Res., 24:82 (1986).

SUMMARY OF THE INVENTION

The invention relates to peptides covered by the following generic formula:

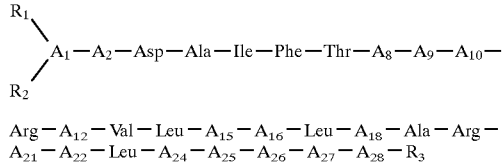

in which
$A_1$ is the D- or L- isomer of an amino acid selected from the group consisting of Tyr and His, or is deleted;
$A_2$ is Aib, or the D- or L- isomer of an amino acid selected from the group consisting of Ala, N-Me-Ala, and Arg;
$A_8$ is Ala, Aib, or Gly;
$A_9$ is Ala, Aib, or Gly;
$A_{10}$ is Phe or p-X-Phe where X is OH, $CH_3$, or a halogen (e.g., F, Cl, Br, or I);
$A_{12}$ is Lys or $N^\epsilon$-X-Lys where X is $C_{1-6}$ alkyl, $C_{1-6}$ acyl, $C_{1-6}$ hydroxyalkyl, or $C_{2-6}$ hydroxyacyl;
$A_{15}$ is Ala, Aib, or Gly;
$A_{16}$ is Ala, Aib, or Gly;
$A_{18}$ is Ala, Aib, or Gly;
$A_{21}$ is Lys or $N^\epsilon$-X-Lys where X is $C_1$–$C_6$ alkyl, $C_1$–$C_6$ acyl, $C_1$–$C_6$ hydroxyalkyl, or $C_2$–$C_6$ hydroxyacyl;
$A_{22}$ is Ala, Aib, Gly, Leu, Ile, Val, Nle, Nva, or Abu;
$A_{24}$ is Ala, Aib, Gaba, Gly or His;
$A_{25}$ is Ala, Aib, Gaba, Gly, His, or is deleted;
$A_{26}$ is Ala, Aib, Gaba, Gly, His, or is deleted;
$A_{27}$ is Ala, Aib, Gly, Leu, Ile, Val, Nle, Nva, Abu, Gaba, β-Ala, Ava, His, or is deleted;
$A_{28}$ is Aib, the D- or L- isomer of Ala, Gaba, His, or is deleted;
each of $R_1$ and $R_2$ is, independently, H, $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, $C_{11-20}$ hydroxynaphthylalkyl, or $COE_1$ where $E_1$ is $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, or $C_{11-20}$ hydroxynaphthylalkyl; and
$R_3$ is OH, $NH_2$, $C_{1-12}$ alkoxy, or $NH.Y.CH_2.Z$ where Y is a $C_{1-12}$ hydrocarbon moiety (divalent, e.g., straight or branched alkyl group) and Z is H, OH, $CO_2H$, or $CONH_2$; or a pharmaceutically acceptable salt thereof.

Below are examples of the peptides of this invention as covered by the above formula:

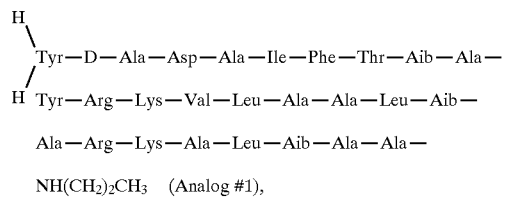

(Analog #1),

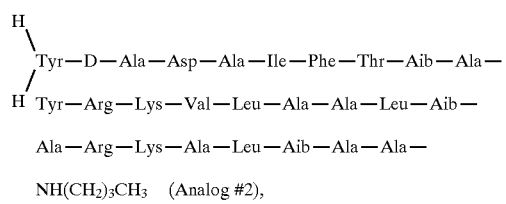

(Analog #2),

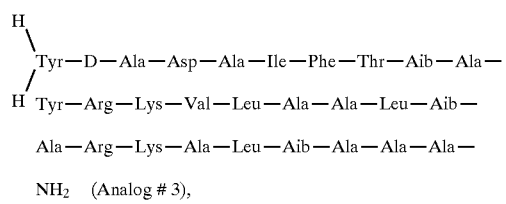

(Analog #3),

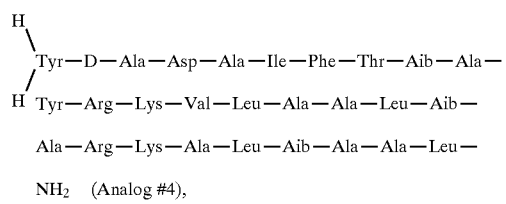

(Analog #4),

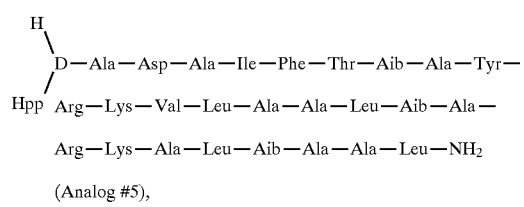

(Analog #5),

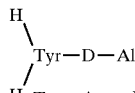
(Analog #6),
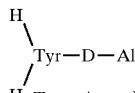
(Analog #7),
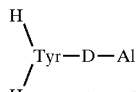
(Analog #8),
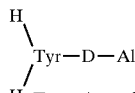
(Analog #9),
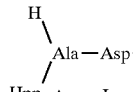
(Analog #10, SEQ ID NO:8),
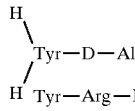
(Analog #11),
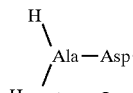
(Analog #12, SEQ ID NO:1),
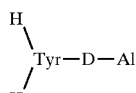
(Analog #13),
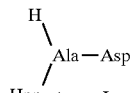
(Analog #14, SEQ ID NO:2),
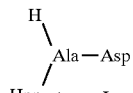
(Analog #15, SEQ ID NO:3),
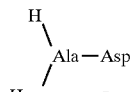
(Analog #16, SEQ ID NO:4),
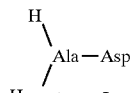
(Analog #17, SEQ ID NO:5),
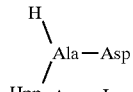
(Analog #18, SEQ ID NO:6),
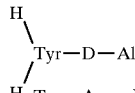
(Analog #19),
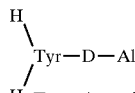
(Analog #20),
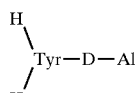
(Analog #21),

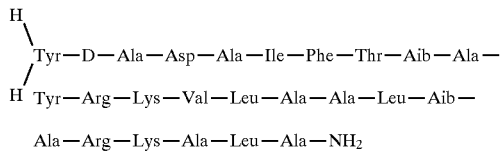

(Analog #22),

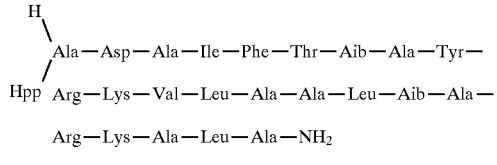

(Analog #23, SEQ ID NO:7),

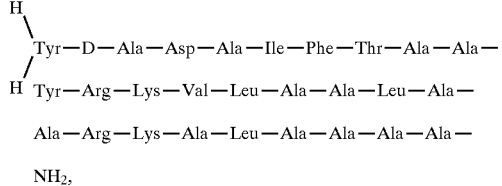

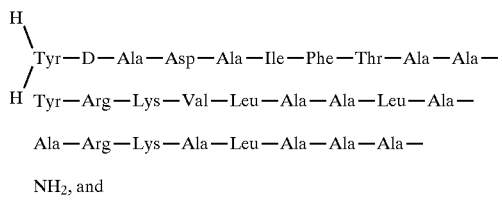

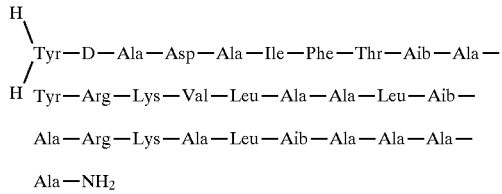

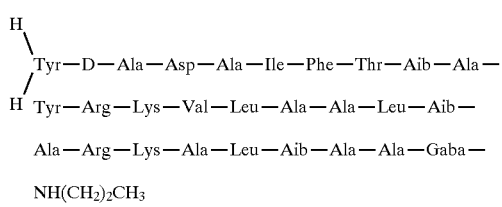

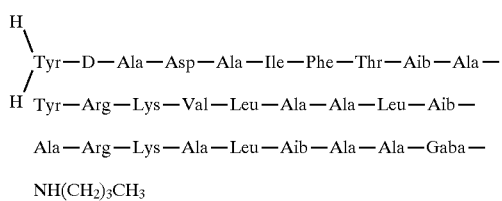

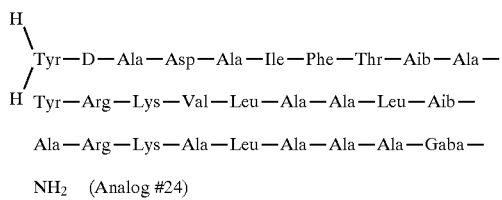

(Analog #24)

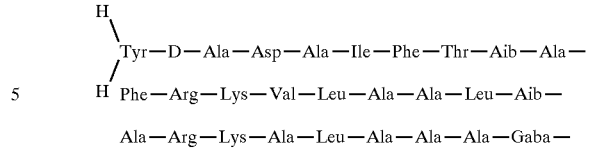

(Analog #25)

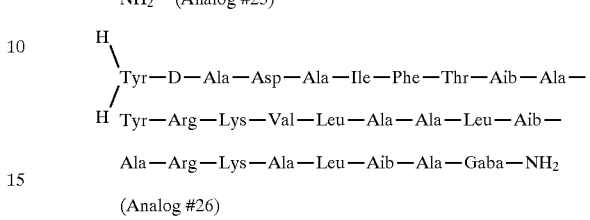

(Analog #26)

With the exception of the N-terminal amino acid, Gaba, β-Ala, and Ava, all abbreviations (e.g., Ala or $A_2$) of amino acids in this disclosure stand for the structure of an α-amino acid residue —NH—CH(R)—CO—, wherein R is a side chain of an amino acid (e.g., $CH_3$ for Ala). Similar structures are intended for the non-α-amino acid residues Gaba, β-Ala, and Ava. On the other hand, for the N-terminal amino acid, the abbreviation stands for the structure of =N—CH(R)—CO—, wherein R is a side chain determinant of an amino acid. N-Me-Ala, Nle, Nva, Abu, Gaba, β-Ala, Ava, and Aib are respective abbreviations of the following α-amino acids: N-methyl-alanine, norleucine, norvaline, α-aminobutyric acid, γ-aminobutyric acid (4-aminobutanoic acid), β-alanine (3-aminopropionic acid), 6-aminovaleric acid (5-aminopentanoic acid), and α-aminoisobutyric acid. $N^\epsilon$-X-Lys stands for the amino acid Lys wherein a hydrogen of the epsilon amino group is replaced by X. Where the amino acid residue is optically active, it is the L-isomer that is intended unless otherwise specified. Also, in the above generic formula, hydroxyalkyl, hydroxyacyl, hydroxyphenylalkyl, and hydroxynaphthylalkyl may contain 1–4 hydroxy substituents, and $COE_1$ stands for —C=O.$E_1$. Examples of —C=O.$E_1$ include, but are not limited to, p-hydroxyphenylpropionyl (or Hpp, i.e., —C=O.$CH_2$—$CH_2$—$C_6H_4$—OH) and phenylpropionyl.

The peptides of the invention can be used to stimulate the release of growth hormone in a subject (a mammal such as a human patient). Thus, the peptides are useful in the treatment of physiological conditions in which growth hormone is of benefit, e.g., those patients who lack adequate endogenous growth hormone production such as the elderly. The peptides of the invention can be used to stimulate linear growth in patients of short stature, e.g., growth hormone deficient children. Other uses include the stimulation of tissue growth (e.g., skeletal, cell, and organ growth), protein metabolism, carbohydrate metabolism, lipid metabolism, mineral metabolism, and connective tissue metabolism, all of which lead to improved physical strength and well-being. The peptides of the invention can also be used in the treatment of catabolic states (e.g., recovery from infection, surgery, and malnutrition), the stimulation of immune function, and enhancement of natural sleep patterns. The peptides of the invention can also be used in stimulating the growth of animals (e.g., livestock).

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), polymeric acids (e.g., tannic acid, carboxymethyl cellulose, polylactic, polyglycolic, or copolymers of polylacticglycolic acids).

A therapeutically effective amount of a peptide of this invention and a pharmaceutically acceptable carrier substance (e.g., magnesium carbonate, lactose, or a phospholipid with which the therapeutic compound can form a micelle) together form a therapeutic composition (e.g., a pill, tablet, capsule, or liquid) for administration (e.g., orally, intravenously, transdermally, pulmonarily, vaginally, subcutaneously, nasally, iontophoretically, or by intratracheally) to a subject in need of the peptide. The pill, tablet, or capsule can be coated with a substance capable of protecting the composition from the gastric acid or intestinal enzymes in the subject's stomach for a period of time sufficient to allow the composition to pass undigested into the subject's small intestine. The therapeutic composition can also be in the form of a biodegradable or nonbiodegradable sustained release formulation for subcutaneous or intramuscular administration. See, e.g., U.S. Pat. Nos. 3,773,919 and 4,767,628 and PCT Application No. WO 94/00148. Continuous administration can also be obtained using an implantable or external pump (e.g., INFUSAID™ pump) to administer the therapeutic composition. The peptide can be administered prior to bedtime of the patient.

The dose of a peptide of the present invention for treating the above-mentioned diseases or disorders varies depending upon the manner of administration, the age and the body weight of the subject, and the condition of the subject to be treated, and ultimately will be decided by the attending physician or veterinarian. Such an amount of the peptide as determined by the attending physician or veterinarian is referred to herein as a "therapeutically effective amount."

Also contemplated within the scope of this invention is a peptide covered by the above generic formula for use in treating diseases or disorders associated with growth hormone deficiencies.

The GRF analogs of this invention do not possess the undesirable arginine and methionine residues at the C-terminus thereby, both decreasing the cost of synthesis and enhancing the stability of the peptides.

Other features and advantages of the present invention will be apparent from the detailed description and from the claims.

DETAILED DESCRIPTION OF THE INVENTION

The synthesis and use of GRF analogs of this invention are well within the ability of a person of ordinary skill in the art. Unless defined otherwise, all technical and scientific terms used herein have the same meaning as commonly understood by one of ordinary skill in the art to which this invention belongs. Also, all publications, patent applications, patents, and other references mentioned herein are incorporated by reference.

It is believed that one skilled in the art can, based on the description herein, utilize the present invention to its fullest extent. The following specific embodiments are, therefore, to be construed as merely illustrative, and not limitative of the remainder of the disclosure in any way whatsoever.
Synthesis The peptides of the invention can be prepared by standard solid phase synthesis. See, e.g., Stewart, J. M., et al., Solid Phase Synthesis (Pierce Chemical Co., 2d. ed. 1984). The following is a description of how Analog #3 was prepared. Other peptides of the invention can be prepared in an analogous manner by a person of ordinary skill in the art.

Benzyhydrylamine-polystyrene resin (Advanced ChemTech, Inc., Louisville, Ky.) (1.25 g, 0.5 mmole) in the chloride ion form is placed in the reaction vessel of an Advanced ChemTech peptide synthesizer (ACT 200) programmed to perform the following reaction cycle: (a) methylene chloride; (b) 33% trifluoroacetic acid in methylene chloride (2 times for 1 and 15 min each); (c) methylene chloride; (d) ethanol; (e) methylene chloride; and (f) 10% diisopropylethylamine in methylene chloride.

The neutralized resin was stirred with Boc-Ala and diisopropylcarbodiimide (1.5 mmole each) in methylene chloride for 1 h and the resulting amino acid resin was then cycled through steps (a) to (f) in the above wash program. The following amino acids (1.5 mmole) were then coupled successively by the same procedure: Boc-Ala, Boc-Ala, Boc-Aib, Boc-Leu, Boc-Ala, Boc-Lys(2-Cl-Z), Boc-Arg (Tos), Boc-Ala, Boc-Aib, Boc-Leu, Boc-Ala, Boc-Ala, Boc-Leu, Boc-Val, Boc-Lys(2-Cl-Z), Boc-Arg(Tos), Boc-Tyr (diClBzl), Boc-Ala, Boc-Aib, Boc-Thr(Bzl), Boc-Phe, Boc-Ile, Boc-Ala, Boc-Asp, Boc-D-Ala, Boc-Tyr(diClBzl). After removal of the last Boc group and washing (MeOH) and drying in air at ambient temperature, the completed resin weighed 2.5 g.

The completed resin (2.5 g, 0.5 mmole) was mixed with anisole (5 ml), dithiothreitol (100 mg) and anhydrous hydrogen fluoride (35 ml) at 0° C. and stirred for 45 min. Excess hydrogen fluoride is evaporated rapidly under a stream of dry nitrogen. The free peptide precipitated and was washed with ether. The crude peptide was then dissolved in a minimum volume of 2M acetic acid and eluted on a column (2.5×100 cm) of SEPHADEX® G-50 (Pharmacia, Piscataway, N.J.) using the same solvent. Fractions containing a major component, determined by UV absorption and thin layer chromatography, were then pooled, evaporated to a small volume, applied to a column (2.5×50 cm) of VYDAC™ octadecylsilane silica (10–15 µm) (Separations Group, Hesperia, Calif.), and eluted with a linear gradient of 10–45% acetonitrile in 0.1% trifluoroacetic acid in water.

The collected fractions were examined by thin layer chromatography and analytical high performance liquid chromatography and pooled to give maximum purity. Repeated lyophilization of the solution from water gave a product of a white, fluffy powder.

The product is found to be homogeneous by high performance gas chromatography (HPLC) and thin layer chromatography (TLC). Amino acid analysis of an acid hydrolysate confirms the composition of the octapeptide. Laser desorption MS gave a molecular weight of 2793 in agreement with the calculated value.

The peptide of the invention can also be prepared by fragment condensation methodology wherein fragments of the peptide are synthesized separately and subsequently coupled. This methodology generally results in a significantly higher synthesis yield. Preferably, the amino acid of the fragment coupled to resin is not optically active (e.g., Aib or Gly), thereby eliminating the possibility of racemization upon cleavage from the resin. The following is a description of the synthesis of Analog #2 by fragment condensation methodology. Other peptides of the invention can be prepared in an analogous manner by a person of ordinary skill in the art.

Boc-Aib-O—$CH_3$-polystyrene-divinylbenzene copolymer (Merrifield) resin (2.5 g, 1.0 mmole) was placed in the reaction vessel of an Advanced ChemTech (ACT 200) peptide synthesizer programmed to perform the following reaction cycle: (a) methylene chloride; (b) 33% trifluoroacetic acid in methylene chloride (2 times for 1 and 15 min each); (c) methylene chloride; (d) ethanol; (e) methylene chloride; and (f) 10% diisopropylethylamine in methylene chloride.

The neutralized resin is stirred with Boc-$N^G$-tosyl-Arg and diisopropylcarbodiimide (1.5 mmole each) in methylene chloride for 1 h and the resulting amino acid resin was then cycled through steps (a) to (f) in the above wash program. The following amino acids (1.5 mmole) were then coupled successively by the same procedure: Boc-Leu, Boc-Ala, Boc-Lys(Z), Boc-Arg(Tos), and Boc-Ala.

The completed resin weighed 3.4 g and was suspended in tetrahydrofuran (THF) (50 ml) and saturated $K_2CO_3$ (20 ml). Tetrabutylammonium hydrogensulfate (2.8 g) was then added and the mixture stirred at 50° C. (18 h). THF was removed under vacuum and the remaining solution neutralized with solid $KHSO_4$ whereupon a buff colored oil precipitates. This oil was extracted into n-BuOH and repeatedly washed with water and evaporated to give Boc-Ala-Arg (Tos)-Lys(Z)-Ala-Leu-Aib-OH as a white powder (1.08 g, 0.96 mmole, 96%). The material gave one spot upon TLC on $SiO_2$ plates ($CHCl_3$:MeOH:$H_2O$:45:10:1).

Boc-Ala-O—$CH_3$-polystyrene-divinylbenzene copolymer (Merrifield) resin (1.0 g, 0.5 mmole) was placed in the reaction vessel of an Advanced ChemTech peptide synthesizer programmed to perform the following reaction cycle: (a) methylene chloride; (b) 33% trifluoroacetic acid in methylene chloride (2 times for 1 and 15 min each); (c) methylene chloride; (d) ethanol; (e) methylene chloride; and (f) 10% diisopropylethylamine in methylene chloride.

The neutralized resin was stirred with Boc-Ala and diisopropylcarbodiimide (1.5 mmole each) in methylene chloride for 1 h and the resulting amino acid resin was then cycled through steps (a) to (f) in the above wash program. Boc-Ala (1.5 mmoles) was then coupled and the resin subjected to the same cycle of events. The fragment Boc-Ala-Arg(Tos)-Lys (Z)-Ala-Leu-Aib-OH (750 mg, 0.74 mmole), synthesized above, was then coupled to this resin in the presence of HBTU (170 mg), HOBt (170 mg), and 10% diisopropylethylamine/DMF (3 ml). The following amino acids (1.5 mmole) are then coupled successively in the presence of diisopropylcarbodiimide (1.5 mmole each) in methylene chloride for 1 h: Boc-Aib, Boc-Leu, Boc-Ala, Boc-Ala, Boc-Leu, Boc-Val, Boc-Lys(2-Cl-Z), Boc-Arg (Tos), Boc-Tyr(diClBzl), Boc-Ala, Boc-Aib, Boc-Thr(Bzl), Boc-Phe, Boc-Ile, Boc-Ala, Boc-Asp(FMOC), Boc-D-Ala, Boc-Tyr(diClBzl). The completed resin weighed 1.95 g. The completed resin (0.96 g, 0.25 mmole) was stirred in 20 ml of a 50:50 mixture of dimethylformamide and n-butylamine (18 h). The reaction mixture was evaporated to an oil to which water was added to give a white powder (0.5 g).

This powder was subjected to cleavage with hydrogen fluoride and column purification as described above. Repeated lyophilization of the solution from water gave the desired product as a white, fluffy powder. The product was found to be homogeneous by HPLC and TLC. Amino acid analysis of an acid hydrolysate confirms the composition of the octapeptide. Laser desorption MS gave a MW of 2736 in agreement with the calculated value.

The substituents $R_1$ and $R_2$ of the above generic formula may be attached to the free amine of the N-terminal amino acid by standard methods known in the art. For example, alkyl groups, e.g., $C_{1-12}$ alkyl, may be attached using reductive alkylation. Hydroxyalkyl groups, e.g., $C_{1-12}$ hydroxyalkyl, may also be attached using reductive alkylation wherein the free hydroxy group is protected with a t-butyl ester. Acyl groups, e.g., $COE_1$, may be attached by coupling the free acid, e.g., $E_1COOH$, to the free amine of the N-terminal amino acid by mixing the completed resin with 3 molar equivalents of both the free acid and diisopropylcarbodiimide in methylene chloride for one hour and cycling the resulting resin through steps (a) to (f) in the above wash program. If the free acid contains a free hydroxy group, e.g., p-hydroxyphenylpropionic acid, then the coupling should be performed with an additional 3 molar equivalents of HOBT.

The full names for the abbreviations used in the above description of synthesis are as follows: Boc for t-butyloxycarbonyl, Tos for tosyl, $N^G$-Tosyl for tosyl at guanidyl site, Z for benzyloxycarbonyl, Bzl for benzyl, HBTU for (1H-benzotriazol-1-yl)-1,1,3,3,-tetramethyluronium hexafluorophosphate, HOBT for hydroxybenzotriazole, and FMOC for 9-fluorenylmethyloxycarbonyl.

Activities

Pituitaries from adult Charles River CD® male rats (Charles River Laboratories, Wilmington, Mass.) housed under controlled conditions (lights on from 0500–1900 h) were dispersed and cultured using aseptic technique by modification of previously described methods. See Hoefer, M. T., et al., Mol. Cell Endocrinol. 35:229 (1984); Ben-Jonathan, N., et al., Methods Enzymol. 103:249 (1983); and Heiman, M. L., et al., Endocrinology 116:410 (1985). Pituitaries were removed from decapitated rats, sectioned, and then placed into a siliconized, liquid scintillation vial containing 2 ml 0.2% trypsin (Worthington Biochemicals, Freehold, N.J.) in sterile-filtered Krebs-Ringer bicarbonate buffer supplemented with 1% bovine serum albumin, 14 mM glucose, modified Eagle medium (MEM) vitamin solution and MEM amino acids (Gibco Laboratories, Grand Island, N.Y.) (KRBGA). All glassware was siliconized as described by Sayers, et al., Endocrinology 88:1063 (1971). The fragments were incubated in a water bath for 35 min. at 37° C. with agitation. The vial contents then were poured into a scintillation vial containing 2 ml 0.1% DNase (Sigma Chemical Co., St. Louis, Mo.) in KRBGA and incubated for 2 min. at 37° C. with agitation. After incubation the tissue was decanted into a 15 ml centrifuge tube and allowed to settle. Medium was discarded, and pituitary sections were washed 3 times with 1 ml fresh KRBGA. The cells were then dispersed in 2 ml 0.05% LBI (lima bean trypsin inhibitor, Worthing Biochemicals) by gently drawing the fragments into and expelling them out of a siliconized, fire-polished Pasteur pipette. Dispersed cells were then filtered through a 630 µm diameter Nylon mesh (Tetko, Elmsford, N.Y.) into a fresh 15 ml centrifuge tube. The first tube was rinsed with an additional 2 ml LBI which was also transferred to the second tube with filtering.

The dispersed cells were then further diluted with approximately 15 ml sterile-filtered Dulbecco's modified Eagle medium (Gibco), which was supplemented with 2.5% fetal calf serum (Gibco), 3% horse serum (Gibco), 10% fresh rat serum (stored on ice for no longer than 1 h) from the pituitary donors, 1% MEM nonessential amino acids (Gibco), gentamicin (10 ng/ml; Sigma) and nystatin (10,000 U/ml; Gibco). The cells were poured into a 50 ml round-bottomed glass extraction flask with a large diameter opening. Cells were counted with a hemacytometer (approximately 2,000,000 cells per pituitary) and randomly plated at a density of about 200,000 cells per well (Co-star cluster 24; Rochester Scientific Co., Rochester, N.Y.). The plated cells were maintained in the above Dulbecco's medium in a humidified atmosphere of 95% air and 5% $CO_2$ at 37° C. for 96 h.

In preparation for a hormone challenge, the cells were washed 3 times with medium 199 (Gibco) to remove old medium and floating cells. Each dose of a test compound (diluted in siliconized test tubes) was tested in the presence of 0.1 nM somatostatin-14 in triplicate or quadruplicate wells in a total volume of 1 ml medium 199 containing 1% BSA (fraction V; Sigma Chemical Co.). After 3 h at 37° C. in an air/carbon dioxide atmosphere (95/5%), the medium was removed and stored at −20° C. until assayed for growth hormone content. Growth hormone content was determined by standard radioimmunoassay for rat growth hormone. The components for the radioimmunoassay of rat GH including antiserum, GH for radioiodination, and GH reference preparation as well as procedure was obtained from the National Hormone and Pituitary Program (via Ogden Biosciences Corp., Rockville, Md.). The $EC_{50}$, the concentration of test compound required to simulate 50 percent of maximal growth hormone release, for each test compound was calculated and normalized to the $EC_{50}$ value of hGRF(1–29)$NH_2$, which was simultaneously tested in each assay as a reference standard to insure the uniformity of the results, utilizing the following formula:

Normalized $EC_{50}$ of Test Compound=$EC_{50}$ of hGRF(1–29)$NH_2$/$EC_{50}$ of Test Compound The GH release potency of the standard, hGRF(1–26)$NH_2$, and ten test compounds of the invention are listed in Table I. The relative GH release potency was calculated by the following formula:

Relative GH Release Potency=Normalized $EC_{50}$ of hGRF(1–26)$NH_2$/Normalized $EC_{50}$ of Test Compound As the data in Table I indicates, GRF analogs of the present invention are more potent than hGRF(1–26)$NH_2$. For example, Analog #1, Analog #2, and Analog #8, all of which contain 26 amino acid residues, are, respectively, 400, 420, and 130 times more potent than the standard peptide hGRF (1–26)$NH_2$, which also contains 26 amino acid residues.

TABLE I

| Compound | Relative GH Release Potency |
| --- | --- |
| hGRF(1-26)$NH_2$ | 1 |
| Analog #1 | 400 |
| Analog #2 | 420 |
| Analog #3 | 760 |
| Analog #4 | 470 |
| Analog #5 | 240 |
| Analog #6 | 1000 |
| Analog #7 | 560 |
| Analog #8 | 130 |
| Analog #9 | 500 |
| Analog #10 | 1100 |
| Analog #11 | 1400 |
| Analog #12 | 1100 |
| Analog #13 | 700 |
| Analog #14 | 610 |
| Analog #15 | 560 |
| Analog #16 | 36 |
| Analog #17 | 330 |
| Analog #18 | 220 |
| Analog #19 | 560 |
| Analog #20 | 550 |
| Analog #21 | 91 |
| Analog #22 | 27 |
| Analog #23 | 27 |
| Analog #24 | 1800 |
| Analog #25 | 890 |
| Analog #26 | 230 |

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( C ) STRANDEDNESS: Not Relevant
        ( D ) TOPOLOGY: both ( i i ) MOLECULE TYPE: protein ( i x ) FEATURE:
        ( D ) OTHER INFORMATION: The amino group of Ala at position 1 is substituted with p-hydroxyphenylpropionyl; Xaa at each of positions 7, 17 and 23 is α-aminoisobutyric acid; and the carboxyl group of Ala at position 25 is amidated, e.g., COyNH2 instead of COyOH.

( x i ) SEQUENCE DESCRIPTION: SEQ ID NO:1:

```
Ala  Asp  Ala  Ile  Phe  Thr  Xaa  Ala  Tyr  Arg  Lys  Val  Leu  Ala  Ala  Leu
 1                   5                        10                       15

Xaa  Ala  Arg  Lys  Ala  Leu  Xaa  Ala  Ala
              20                       25
```

( 2 ) INFORMATION FOR SEQ ID NO:2:

( i ) SEQUENCE CHARACTERISTICS:
    ( A ) LENGTH: 26 amino acids
    ( B ) TYPE: amino acid
    ( C ) STRANDEDNESS: Not Relevant
    ( D ) TOPOLOGY: both ( i i ) MOLECULE TYPE: protein ( i x ) FEATURE:
    ( D ) OTHER INFORMATION: The amino group of Ala at position 1
      is substituted with p-hydroxyphenylpropionyl; Xaa at each
      of positions 7, 17 and 23 is α-aminoisobutyric acid; and
      the carboxyl group of Ala at position 26 is amidated,
      e.g., COyNH2 instead of COyOH.

( x i ) SEQUENCE DESCRIPTION: SEQ ID NO:2:

Ala Asp Ala Ile Phe Thr Xaa Ala Tyr Arg Lys Val Leu Ala Ala Leu
1               5                   10                  15

Xaa Ala Arg Lys Ala Leu Xaa Ala Ala Ala
            20              25

( 2 ) INFORMATION FOR SEQ ID NO:3:

( i ) SEQUENCE CHARACTERISTICS:
    ( A ) LENGTH: 26 amino acids
    ( B ) TYPE: amino acid
    ( C ) STRANDEDNESS: Not Relevant
    ( D ) TOPOLOGY: both ( i i ) MOLECULE TYPE: protein ( i x ) FEATURE:
    ( D ) OTHER INFORMATION: The amino group of Ala at position 1
      is substituted with p-hydroxyphenylpropionyl; Xaa at
      each of positions 7, 17 and 23 is α-aminoisobutyric
      acid; and the carboxyl group of Ala at position 26 is
      amidated, e.g., COyNH2 instead of COyOH.

( x i ) SEQUENCE DESCRIPTION: SEQ ID NO:3:

Ala Asp Ala Ile Phe Thr Xaa Ala Phe Arg Lys Val Leu Ala Ala Leu
1               5                   10                  15

Xaa Ala Arg Lys Ala Leu Xaa Ala Ala Ala
            20              25

( 2 ) INFORMATION FOR SEQ ID NO:4:

( i ) SEQUENCE CHARACTERISTICS:
    ( A ) LENGTH: 25 amino acids
    ( B ) TYPE: amino acid
    ( C ) STRANDEDNESS: Not Relevant
    ( D ) TOPOLOGY: both ( i i ) MOLECULE TYPE: protein ( i x ) FEATURE:
    ( D ) OTHER INFORMATION: The amino group of Ala at position 1
      is substituted with p-hydroxyphenylpropionyl; Xaa at each
      of positions 7, 17 and 23 is α-aminoisobutyric acid; and
      the carboxyl group of Ala at position 25 is amidated,
      e.g., COyNH2 instead of COyOH.

( x i ) SEQUENCE DESCRIPTION: SEQ ID NO:4:

Ala Asp Ala Ile Phe Thr Xaa Ala Tyr Arg Lys Val Leu Ala Ala Leu
1               5                   10                  15

Xaa Ala Arg Lys Ala Leu Xaa Ala Ala
            20              25

( 2 ) INFORMATION FOR SEQ ID NO:5:

( i ) SEQUENCE CHARACTERISTICS:
        ( A ) LENGTH: 25 amino acids
        ( B ) TYPE: amino acid
        ( C ) STRANDEDNESS: Not Relevant
        ( D ) TOPOLOGY: both ( i i ) MOLECULE TYPE: protein ( i x ) FEATURE:
        ( D ) OTHER INFORMATION: The amino group of Ala at position 1
            is substituted with p-hydroxyphenylpropionyl; Xaa at each
            of positions 7, 17 and 23 is α-aminoisobutyric acid; and
            the carboxyl group of Ala at position 25 is amidated,
            e.g., COyNH(CH2)3CH3 instead of COyOH.

( x i ) SEQUENCE DESCRIPTION: SEQ ID NO:5:

```
Ala  Asp  Ala  Ile  Phe  Thr  Xaa  Ala  Tyr  Arg  Lys  Val  Leu  Ala  Ala  Leu
1                   5                        10                       15

Xaa  Ala  Arg  Lys  Ala  Leu  Xaa  Ala  Ala
               20                       25
```

( 2 ) INFORMATION FOR SEQ ID NO:6:

( i ) SEQUENCE CHARACTERISTICS:
        ( A ) LENGTH: 24 amino acids
        ( B ) TYPE: amino acid
        ( C ) STRANDEDNESS: Not Relevant
        ( D ) TOPOLOGY: both ( i i ) MOLECULE TYPE: protein ( i x ) FEATURE:
        ( D ) OTHER INFORMATION: The amino group of Ala at position 1
            is substituted with p-hydroxyphenylpropionyl; Xaa at
            each of positions 7, 17 and 23 is α-aminoisobutyric
            acid; and the carboxyl group of Ala at position 24 is
            amidated, e.g., COyNH(CH2)3CH3 instead of COyOH.

( x i ) SEQUENCE DESCRIPTION: SEQ ID NO:6:

```
Ala  Asp  Ala  Ile  Phe  Thr  Xaa  Ala  Tyr  Arg  Lys  Val  Leu  Ala  Ala  Leu
1                   5                        10                       15

Xaa  Ala  Arg  Lys  Ala  Leu  Xaa  Ala
               20
```

( 2 ) INFORMATION FOR SEQ ID NO:7:

( i ) SEQUENCE CHARACTERISTICS:
        ( A ) LENGTH: 23 amino acids
        ( B ) TYPE: amino acid
        ( C ) STRANDEDNESS: Not Relevant
        ( D ) TOPOLOGY: both ( i i ) MOLECULE TYPE: protein ( i x ) FEATURE:
        ( D ) OTHER INFORMATION: The amino group of Ala at position 1
            is substituted with p-hydroxyphenylpropionyl; Xaa at each
            of positions 7 and 17 is α-aminoisobutyric acid; and the
            carboxyl group of Ala at position 23 is amidated, e.g.,
            COyNH2 instead of COyOH.

( x i ) SEQUENCE DESCRIPTION: SEQ ID NO:7:

```
Ala  Asp  Ala  Ile  Phe  Thr  Xaa  Ala  Tyr  Arg  Lys  Val  Leu  Ala  Ala  Leu
1                   5                        10                       15

Xaa  Ala  Arg  Lys  Ala  Leu  Ala
               20
```

( 2 ) INFORMATION FOR SEQ ID NO:8:

```
        ( i ) SEQUENCE CHARACTERISTICS:
                ( A ) LENGTH: 27 amino acids
                ( B ) TYPE: amino acid
                ( C ) STRANDEDNESS: Not Relevant
                ( D ) TOPOLOGY: both ( i i ) MOLECULE TYPE: protein ( i x ) FEATURE:
                ( D ) OTHER INFORMATION: The amino group of Ala at position 1
                        is substituted with p-hydroxyphenylpropionyl; Xaa at
                        each of positions 7, 17 and 23 is α-aminoisobutyric acid;
                        Xaa at position 26 is Nle; and the carboxyl group of Ala
                        at position 27 is amidated, e.g., COyNH2 instead of
                        COyOH.

( x i ) SEQUENCE DESCRIPTION: SEQ ID NO:8:

Ala  Asp  Ala  Ile  Phe  Thr  Xaa  Ala  Tyr  Arg  Lys  Val  Leu  Ala  Ala  Leu
 1                    5                       1 0                          1 5

Xaa  Ala  Arg  Lys  Ala  Leu  Xaa  Ala  Ala  Xaa  Ala
              2 0                   2 5
```

What is claimed is:

1. A peptide of the formula:

in which $A_1$ is the D- or L- isomer of an amino acid selected from the group consisting of Tyr and His, or is deleted;

$A_2$ is Aib, or the D- or L- isomer of an amino acid selected from the group consisting of Ala, N-Me-Ala, and Arg;

$A_8$ is Ala, Aib, or Gly;

$A_9$ is Ala, Aib, or Gly;

$A_{10}$ is Phe or p-X-Phe where X is OH, $CH_3$, or a halogen;

$A_{12}$ is Lys or $N^\epsilon$-X-Lys where X is $C_{1-6}$ alkyl, $C_{1-6}$ acyl, $C_{1-6}$ hydroxyalkyl, or $C_{2-6}$ hydroxyacyl;

$A_{15}$ is Ala, Aib, or Gly;

$A_{16}$ is Ala, Aib, or Gly;

$A_{18}$ is Ala, Aib, or Gly;

$A_{21}$ is Lys or $N^\epsilon$-X-Lys where X is $C_1$–$C_6$ alkyl, $C_1$–$C_6$ acyl, $C_1$-$c_6$ hydroxyalkyl, or $C_2$–$C_6$ hydroxyacyl;

$A_{22}$ is Ala, Aib, Gly, Leu, Ile, Val, Nle, Nva, or Abu;

$A_{24}$ is Ala, Aib, Gaba, Gly or His;

$A_{25}$ is Ala, Aib, Gaba, Gly, His or is deleted;

$A_{26}$ is Ala, Aib, Gaba, Gly, His or is deleted;

$A_{27}$ is Ala, Aib, Gly, Leu, Ile, Val, Nle, Nva, Abu, Gaba, β-Ala, Ava, His, or is deleted;

$A_{28}$ is Aib, the D- or L- isomer of Ala, Gaba, His, or is deleted;

each of $R_1$ and $R_2$ is, independently, H, $C_{1-12}$ alkyl, $C_{7-20}$ phenylalkyl, $C_{11-20}$ napthylalkyl, $C_{1-12}$ hydroxyalkyl, $C_{7-20}$ hydroxyphenyl, $C_{11-20}$ hydroxynapthylalkyl, or $COE_1$ where $E_1$ is $C_{1-12}$ alkyl, $C_{7-20}$ phenylalkyl, $C_{11-20}$ napthylalkyl, $C_{1-12}$ hydroxyalkyl, $C_{7-20}$ hydroxyphenylalkyl, or $C_{11-20}$ hydroxynapthylalkyl; and $R_3$ is OH, $NH_2$, $C_{1-12}$ alkoxy, or $NH.Y.CH_2.Z$ where Y is a $C_{1-12}$ hydrocarbon moiety and Z is H, OH, $CO_2H$, or $CONH_2$; or a pharmaceutically acceptable salt thereof.

2. A peptide of claim 1, wherein $A_{25}$ is Ala, $A_{26}$ is Ala, $A_{27}$ is Ala, Aib, Leu, Ile, Val, Nle, Nva, Gaba, or Abu, and $A_{28}$ is Ala.

3. A peptide of claim 2, wherein $A_8$ is Ala or Aib, $A_9$ is Ala, $A_{10}$ is Phe or Tyr, $A_{12}$ is Lys, $A_{15}$ is Ala, $A_{16}$ is Ala, $A_{18}$ is Ala or Aib, $A_{21}$ is Lys, $A_{22}$ is Ala, $A_{24}$ is Ala or Aib, and $A_{27}$ is Ala, Leu, Gaba, or Nle.

4. A peptide of claim 3, wherein $A_8$ is Aib, $A_{18}$ is Aib, and $A_{24}$ is Aib.

5. A peptide of claim 4, wherein $A_1$ is Tyr, and $A_2$ is D-Ala or L-Ala.

6. A peptide of claim 4, wherein $A_1$ is deleted, $A_2$ is D-Ala or L-Ala, $R_1$ is H, and $R_2$ is $COE_1$.

7. A peptide of claim 3, wherein $R_3$ is $NH.Y.CH_2.Z$.

8. A peptide of claim 1, wherein $A_{28}$ is deleted.

9. A peptide of claim 8, wherein $A_{25}$ is Ala, $A_{26}$ is Ala, and $A_{27}$ is Ala, Aib, Leu, Ile, Val, Nle, Nva, Gaba, or Abu.

10. A peptide of claim 9, wherein $A_8$ is Ala or Aib, $A_9$ is Ala, $A_{10}$ is Phe or Tyr, $A_{12}$ is Lys, $A_{15}$ is Ala, $A_{16}$ is Ala, $A_{18}$ is Ala or Aib, $A_{21}$ is Lys, $A_{22}$ is Ala, $A_{24}$ is Ala or Aib, and $A_{27}$ is Ala, Leu, Gaba, or Nle.

11. A peptide of claim 10, wherein $A_8$ is Aib, $A_{18}$ is Aib, and $A_{24}$ is Aib.

12. A peptide of claim 11, wherein $A_1$ is Tyr, and $A_2$ is D-Ala or L-Ala.

13. A peptide of claim 11, wherein $A_1$ is deleted, $A_2$ is D-Ala or L-Ala, $R_1$ is H, and $R_2$ is $COE_1$.

14. A peptide of claim 10, wherein $R_3$ is $NH.Y.CH_2.Z$.

15. A peptide of claim 1, wherein $A_{27}$ is deleted and $A_{28}$ is deleted.

16. A peptide of claim 15, wherein $A_{25}$ is Ala, and $A_{26}$ is Ala.

17. A peptide of claim 16, wherein $A_8$ is Ala or Aib, $A_9$ is Ala, $A_{10}$ is Phe or Tyr, $A_{12}$ is Lys, $A_{15}$ is Ala, $A_{16}$ is Ala, $A_{18}$ is Ala or Aib, $A_{21}$ is Lys, $A_{22}$ is Ala, and $A_{24}$ is Ala or Aib.

18. A peptide of claim 17, wherein $A_8$ is Aib, $A_{18}$ is Aib, and $A_{24}$ is Aib.

19. A peptide of claim 18, wherein $A_1$ is Tyr, and $A_2$ is D-Ala or L-Ala.

20. A peptide of claim 18, wherein $A_1$ is deleted, $A_2$ is D-Ala or L-Ala, $R_1$ is H, and $R_2$ is $COE_1$.

21. A peptide of claim 17, wherein $R_3$ is $NH.Y.CH_2.Z$.

22. A peptide of claim 1 of the formula:

H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Aib—Ala—Ala—NH(CH$_2$)$_2$CH$_3$

H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Aib—Ala—Ala—NH(CH$_2$)$_3$CH$_3$

H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Aib—Ala—Ala—Ala—NH$_2$

H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Aib—Ala—Ala—Leu—NH$_2$

\D—Ala—Asp—Ala—Ile—Phe—Thr—Aib—Ala—Tyr—
Hpp/
   Arg—Lys—Val—Leu—Ala—Ala—Leu—Aib—Ala—
   Arg—Lys—Ala—Leu—Aib—Ala—Ala—Leu—NH$_2$

H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Aib—Ala—Ala—Nle—Ala—NH$_2$

H\
 \Tyr—D—Ala—Asp—Ala—Ile—Phe—Thr—Ala—Ala—
H/
   Tyr—Arg—Lys—Val—Leu—Ala—Ala—Leu—Ala—Ala—
   Arg—Lys—Ala—Leu—Ala—Ala—Ala—Ala—NH$_2$

H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Aib—Ala—Ala—NH$_2$

H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Ala—Ala—Ala—Ala—NH$_2$

\Ala—Asp—Ala—Ile—Phe—Thr—Aib—Ala—Tyr—Arg—
Hpp/
   Lys—Val—Leu—Ala—Ala—Leu—Aib—Ala—Arg—Lys—
   Ala—Leu—Aib—Ala—Ala—Nle—Ala—NH$_2$ (SEQ ID NO: 8),

-continued

H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Aib—Ala—Ala—Gaba—NH$_2$ H\
 \Ala—Asp—Ala—Ile—Phe—Thr—Aib—Ala—Tyr—Arg—
Hpp/
   Lys—Val—Leu—Ala—Ala—Leu—Aib—Ala—Arg—Lys—
   Ala—Leu—Aib—Ala—Ala—Gaba—NH$_2$ (SEQ ID NO: 1), H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Aib—Ala—Ala—Leu—Ala—NH$_2$ H\
 \Ala—Asp—Ala—Ile—Phe—Thr—Aib—Ala—Tyr—Arg—
Hpp/
   Lys—Val—Leu—Ala—Ala—Leu—Aib—Ala—Arg—Lys—
   Ala—Leu—Aib—Ala—Ala—Ala—NH$_2$ (SEQ ID NO: 2), H\
 \Ala—Asp—Ala—Ile—Phe—Thr—Aib—Ala—Phe—Arg—
Hpp/
   Lys—Val—Leu—Ala—Ala—Leu—Aib—Ala—Arg—Lys—
   Ala—Leu—Aib—Ala—Ala—Ala—NH$_2$ (SEQ ID NO: 3), H\
 \Ala—Asp—Ala—Ile—Phe—Thr—Aib—Ala—Tyr—Arg—
Hpp/
   Lys—Val—Leu—Ala—Ala—Leu—Aib—Ala—Arg—Lys—
   Ala—Leu—Aib—Ala—Ala—NH$_2$ (SEQ ID NO: 4), H\
 \Ala—Asp—Ala—Ile—Phe—Thr—Aib—Ala—Tyr—Arg—
Hpp/
   Lys—Val—Leu—Ala—Ala—Leu—Aib—Ala—Arg—Lys—
   Ala—Leu—Aib—Ala—Ala—NH(CH$_2$)$_3$CH$_3$ (SEQ ID NO: 5), H\
 \Ala—Asp—Ala—Ile—Phe—Thr—Aib—Ala—Tyr—Arg—
Hpp/
   Lys—Val—Leu—Ala—Ala—Leu—Aib—Ala—Arg—Lys—
   Ala—Leu—Aib—Ala—NH$_2$(CH$_2$)$_3$CH$_3$ (SEQ ID NO: 6), H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Ala—Ala—Ala—NH$_2$(CH$_2$)$_3$CH$_3$ H\
 \Tyr—D—Ala—Asp—Ala—Ile—Phe—Thr—Aib—Ala—
H/
   Tyr—Arg—Lys—Val—Leu—Ala—Ala—Leu—Aib—Ala—
   Arg—Lys—Ala—Leu—Ala—Ala—Ala—NH$_2$(CH$_2$)$_6$CH$_3$ -continued

```
H
 \
  Tyr—D—Ala—Asp—Ala—Ile—Phe—Thr—Aib—Ala—
 /
H
   Tyr—Arg—Lys—Val—Leu—Ala—Ala—Leu—Aib—Ala—
   Arg—Lys—Ala—Leu—Ala—Ala—NH2
```

```
H
 \
  Tyr—D—Ala—Asp—Ala—Ile—Phe—Thr—Aib—Ala—
 /
H
   Tyr—Arg—Lys—Val—Leu—Ala—Ala—Leu—Aib—Ala—
   Arg—Lys—Ala—Leu—Ala—NH2
```

```
H
 \
  Ala—Asp—Ala—Ile—Phe—Thr—Aib—Ala—Tyr—Arg—
 /
Hpp
   Lys—Val—Leu—Ala—Ala—Leu—Aib—Ala—Arg—Lys—
   Ala—Leu—Ala—NH2 (SEQ ID NO: 7),
```

```
H
 \
  Tyr—D—Ala—Asp—Ala—Ile—Phe—Thr—Aib—Ala—
 /
H
   Tyr—Arg—Lys—Val—Leu—Ala—Ala—Leu—Aib—Ala—
   Arg—Lys—Ala—Leu—Ala—Ala—Ala—Gaba—NH2
(Analog #24)
```

```
H
 \
  Tyr—D—Ala—Asp—Ala—Ile—Phe—Thr—Aib—Ala—
 /
H
   Phe—Arg—Lys—Val—Leu—Ala—Ala—Leu—Aib—Ala—
   Arg—Lys—Ala—Leu—Ala—Ala—Ala—Gaba—NH2
(Analog #25)
```

```
H
 \
  Tyr—D—Ala—Asp—Ala—Ile—Phe—Thr—Aib—Ala—
 /
H
   Tyr—Arg—Lys—Val—Leu—Ala—Ala—Leu—Aib—Ala—
   Arg—Lys—Ala—Leu—Aib—Ala—Gaba—NH2
(Analog #26).
```

23. A peptide of claim 1 of the formula:

```
H
 \
  Tyr—D—Ala—Asp—Ala—Ile—Phe—Thr—Ala—Ala—
 /
H
   Tyr—Arg—Lys—Val—Leu—Ala—Ala—Leu—Ala—Ala—
   Arg—Lys—Ala—Leu—Ala—Ala—Ala—Ala—NH2,
```

```
H
 \
  Tyr—D—Ala—Asp—Ala—Ile—Phe—Thr—Ala—Ala—
 /
H
   Tyr—Arg—Lys—Val—Leu—Ala—Ala—Leu—Ala—Ala—
   Arg—Lys—Ala—Leu—Ala—Ala—Ala—NH2
```

```
H
 \
  Tyr—D—Ala—Asp—Ala—Ile—Phe—Thr—Aib—Ala—
 /
H
   Tyr—Arg—Lys—Val—Leu—Ala—Ala—Leu—Aib—Ala—
   Arg—Lys—Ala—Leu—Aib—Ala—Ala—Ala—Ala—NH2
```

```
H
 \
  Tyr—D—Ala—Asp—Ala—Ile—Phe—Thr—Aib—Ala—
 /
H
   Tyr—Arg—Lys—Val—Leu—Ala—Ala—Leu—Aib—Ala—
   Arg—Lys—Ala—Leu—Aib—Ala—Ala—Gaba—
   NH(CH2)2CH3
```

```
H
 \
  Tyr—D—Ala—Asp—Ala—Ile—Phe—Thr—Aib—Ala—
 /
H
   Tyr—Arg—Lys—Val—Leu—Ala—Ala—Leu—Aib—Ala—
   Arg—Lys—Ala—Leu—Aib—Ala—Ala—Gaba—
   NH(CH2)2CH3.
```

* * * * *